United States Patent
Qi

(10) Patent No.: US 10,765,408 B2
(45) Date of Patent: Sep. 8, 2020

(54) METHODS AND SYSTEMS FOR FERTILITY ESTIMATION

(71) Applicant: Simple Design Ltd., Tortola (GB)

(72) Inventor: Fangfang Qi, Zhengzhou (CN)

(73) Assignee: SIMPLE DESIGN LTD., Tortola (GB)

( * ) Notice: Subject to any disclaimer, the term of this patent is extended or adjusted under 35 U.S.C. 154(b) by 0 days.

(21) Appl. No.: 15/066,895

(22) Filed: Mar. 10, 2016

(65) Prior Publication Data

US 2017/0258455 A1    Sep. 14, 2017

(51) Int. Cl.
*A61B 10/00* (2006.01)
*G06F 3/0481* (2013.01)
*G06F 3/0484* (2013.01)
*A61B 5/00* (2006.01)

(52) U.S. Cl.
CPC ........ *A61B 10/0012* (2013.01); *A61B 5/4306* (2013.01); *G06F 3/04812* (2013.01); *G06F 3/04842* (2013.01)

(58) Field of Classification Search
CPC ............. A61B 10/0012; G06F 3/04812; G06F 3/04842
See application file for complete search history.

(56) References Cited

U.S. PATENT DOCUMENTS

| | | | |
|---|---|---|---|
| 5,836,890 A * | 11/1998 | Jackson | A61B 10/0012 600/551 |
| 2013/0054150 A1* | 2/2013 | Sacks | A61B 10/0012 702/19 |

OTHER PUBLICATIONS

Clue for iOS: App Review https://www.youtube.com/watch?v=ZUgsOBwDOZg, © Mar. 9, 2015.*
https://www.youtube.com/watch?v=9iIPOMVtxBI Dec. 25, 2015 "Clue II Cycle Charting App Review".*
Clue for iOS: App Review (Year: 2015).*

* cited by examiner

*Primary Examiner* — Sherrod L Keaton
(74) *Attorney, Agent, or Firm* — Bayramoglu Law Offices LLC

(57) ABSTRACT

A user-defined range of dates is displayed within a first region, and an interactive cursor is displayed at a first location within the first region, the first location corresponding to a first date within the range of dates. Based at least in part on the first date, a first estimated fertility is determined and displayed in a second region of the display area. A user input is detected at a second location distinct from the first location, the user input corresponding to a user selection of a second date in the range of dates distinct from the first date. In response, the interactive cursor is dynamically moved from the first location to the second location. Based at least in part on the second date, a second estimated fertility is determined, and the first estimated fertility in the second region is replaced with the second estimated fertility.

17 Claims, 10 Drawing Sheets

METHODS AND SYSTEMS FOR FERTILITY ESTIMATION

TECHNICAL FIELD

This application relates generally to menstrual calculators and in particular to methods and interfaces for estimating fertility and tracking menstrual cycle information.

BACKGROUND

A menstrual cycle corresponds to stages of physiological changes through which a woman's body prepares for pregnancy. At each of these stages, and for each day of these stages, a woman's likelihood of pregnancy will vary. Consequently, the ability to accurately and conveniently monitor and predict such variances with day-to-day granularity is important, particularly for the purposes of family planning.

SUMMARY

Accordingly, there is a need for more efficient methods and interfaces for estimating fertility and tracking menstrual cycle information. By manipulating an interactive cursor on a graphical user interface for selecting days of a menstrual cycle, a user's estimated fertility for selected days may be easily determined and dynamically updated.

In accordance with some embodiments, a method is performed at a client device having one or more processors and memory storing instructions for execution by the one or more processors. The method includes displaying a user-defined range of dates within a first region of a display area and an interactive cursor at a first location within the first region, the first location corresponding to a first date within the user-defined range of dates. Based at least in part on the first date, a first estimated fertility is determined and displayed in a second region of the display area distinct from the first region. A user input is detected at a second location within the first region of the display area distinct from the first location, the user input corresponding to a user selection of a second date in the user-defined range of dates distinct from the first date. In response to detecting the user input, the method includes dynamically moving the interactive cursor from the first location to the second location. Based at least in part on the second date, a second estimated fertility is determined, and the first estimated fertility in the second region is replaced with the second estimated fertility.

In accordance with some embodiments, a client device includes a processor and memory storing one or more programs for execution by the processor. The one or more programs include instructions for performing the operations of the method described above. In accordance with some embodiments, a computer-readable storage medium has stored therein instructions that, when executed by the client device, cause the client device to perform the operations of the method described above.

Thus, client devices are provided with more efficient methods for estimating fertility and tracking menstrual cycle information, thereby increasing the effectiveness, efficiency, and user satisfaction with such devices.

BRIEF DESCRIPTION OF THE DRAWINGS

For a better understanding of the various described embodiments, reference should be made to the Description of Embodiments below, in conjunction with the following drawings. Like reference numerals refer to corresponding parts throughout the figures and description.

DESCRIPTION OF EMBODIMENTS

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are used only to distinguish one element from another. For example, a first estimated fertility could be termed a second estimated fertility, and, similarly, a second estimated fertility could be termed a first estimated fertility, without departing from the scope of the various described embodiments. The first estimated fertility and the second estimated fertility are both estimated fertilities, but they are not the same estimated fertility.

The terminology used in the description of the various embodiments described herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

As used herein, the term "exemplary" is used in the sense of "serving as an example, instance, or illustration" and not in the sense of "representing the best of its kind."

Figure 1:
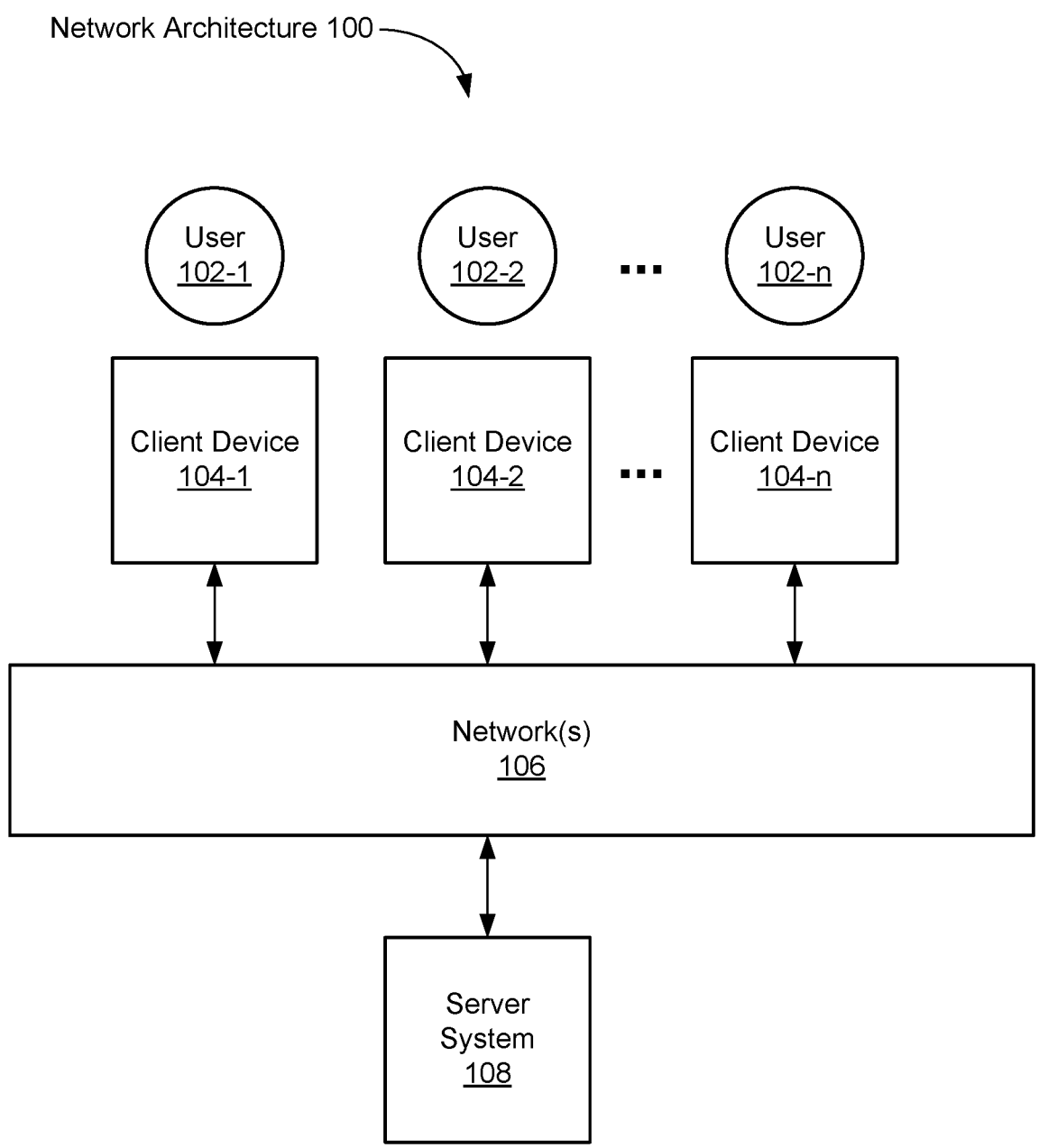
FIG. 1 is a block diagram illustrating an exemplary network architecture of a network for estimating fertility and tracking menstrual cycle information, in accordance with some embodiments.

FIG. 1 is a block diagram illustrating an exemplary network architecture 100 of a network for estimating fertility and tracking menstrual cycle information, in accordance with some embodiments. The network architecture 100 includes a number of client devices (also called "client systems," "client computers," or "clients") 104-1, 104-2, ... 104-n communicably connected to an electronic server system 108 by one or more networks 106 (e.g., the Internet, cellular telephone networks, mobile data networks, other wide area networks, local area networks, metropolitan area networks, and so on). In some embodiments, the one or more networks 106 include a public communication network (e.g., the Internet and/or a cellular data network), a private communications network (e.g., a private LAN or leased lines), or a combination of such communication networks.

In some embodiments, the client devices 104-1, 104-2, ... 104-n are computing devices such as smart watches, personal digital assistants, portable media players, smart phones, tablet computers, 2D gaming devices, 3D (e.g., virtual reality) gaming devices, laptop computers, desktop computers, televisions with one or more processors embedded therein or coupled thereto, in-vehicle information systems (e.g., an in-car computer system that provides navigation, entertainment, and/or other information), and/or other appropriate computing devices that can be used to communicate with the server system 108. In some embodiments, the server system 108 is a single computing device such as a computer server, while in other embodiments, the server system 108 is implemented by multiple computing devices working together to perform the actions of a server system (e.g., cloud computing).

In some embodiments, users 102-1, 102-2, ... 102-n employ the client devices 104-1, 104-2, ... 104-n to access the server system 108 and to participate in a corresponding services provided by the server system 108 (e.g., providing application features and services via the menstrual cycle module 340 for estimating fertility and tracking menstrual cycle information). For example, one or more of the client devices 104-1, 104-2, ... 104-n execute web browser applications that can be used to access services provided by the server system 108. As another example, one or more of the client devices 104-1, 104-2, ... 104-n execute software applications that are specific to services provided by the server system 108 (e.g., applications for estimating fertility and tracking menstrual cycle information, running on an iPhone, Android, or Windows smart phone or tablet).

Figure 2:
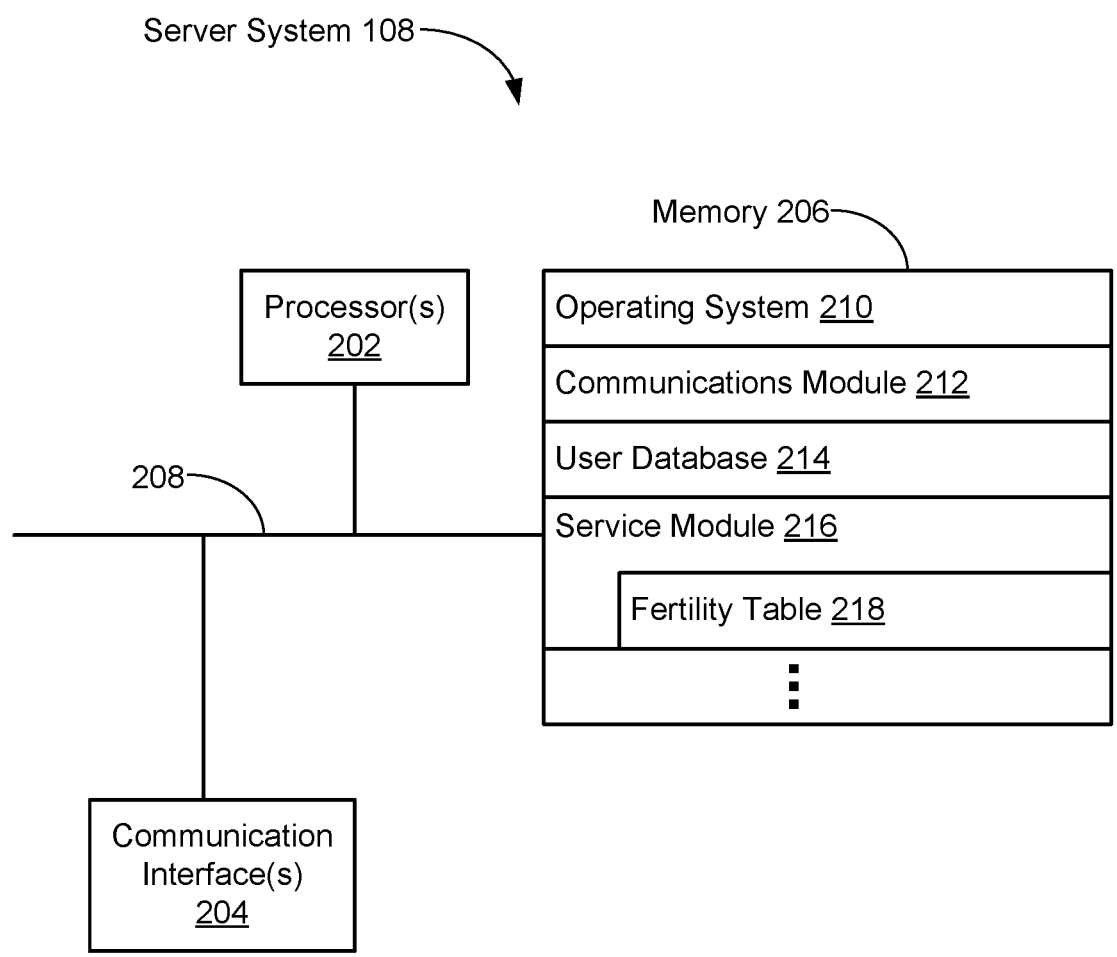
FIG. 2 is a block diagram illustrating an exemplary server system in accordance with some embodiments.

FIG. 2 is a block diagram illustrating an exemplary server system 108 in accordance with some embodiments. The server system 108 typically includes one or more processing units (processors or cores) 202, one or more network or other communications interfaces 204, memory 206, and one or more communication buses 208 for interconnecting these components. The communication buses 208 optionally include circuitry (sometimes called a chipset) that interconnects and controls communications between system components. The server system 108 optionally includes a user interface (not shown). The user interface, if provided, may include a display device and optionally includes inputs such as a keyboard, mouse, trackpad, and/or input buttons. Alternatively or in addition, the display device includes a touch-sensitive surface, in which case the display is a touch-sensitive display.

Memory 206 includes high-speed random-access memory, such as DRAM, SRAM, DDR RAM, or other random-access solid-state memory devices; and may include non-volatile memory, such as one or more magnetic disk storage devices, optical disk storage devices, flash memory devices, and/or other non-volatile solid-state storage devices. Memory 206 may optionally include one or more storage devices remotely located from the processor(s) 202. Memory 206, or alternately the non-volatile memory device(s) within memory 206, includes a non-transitory computer-readable storage medium. In some embodiments, memory 206 or the computer-readable storage medium of memory 206 stores the following programs, modules and data structures, or a subset or superset thereof:

- an operating system 210 that includes procedures for handling various basic system services and for performing hardware dependent tasks;
- a network communication module 212 that is used for connecting the server system 108 to other computers via the one or more communication network interfaces 204 (wired or wireless) and one or more communication networks (e.g., the one or more networks 106)
- a user database 214 for storing user data for users of a service (e.g., service provided by the server system 108 for estimating fertility and tracking menstrual cycle information);
- a service module 216 for estimating fertility and tracking menstrual cycle information (e.g., via the menstrual cycle module 340, FIG. 3), which includes:
  - a fertility table 218 for storing relative estimated fertilities for days and/or stages of a menstrual cycle.

The user database 214 and/or the fertility table 218 store data associated in one or more types of databases, such as graph, dimensional, flat, hierarchical, network, object-oriented, relational, and/or XML databases. User database 214 includes user information, such as user profiles, login information, privacy and other preferences, biographical data, and the like. In some embodiments, for a given user, the user information includes the user's name, profile picture, contact information, birth date, sex, marital status, family status, employment, education background, preferences, interests, and/or other demographic information.

Figure 3:
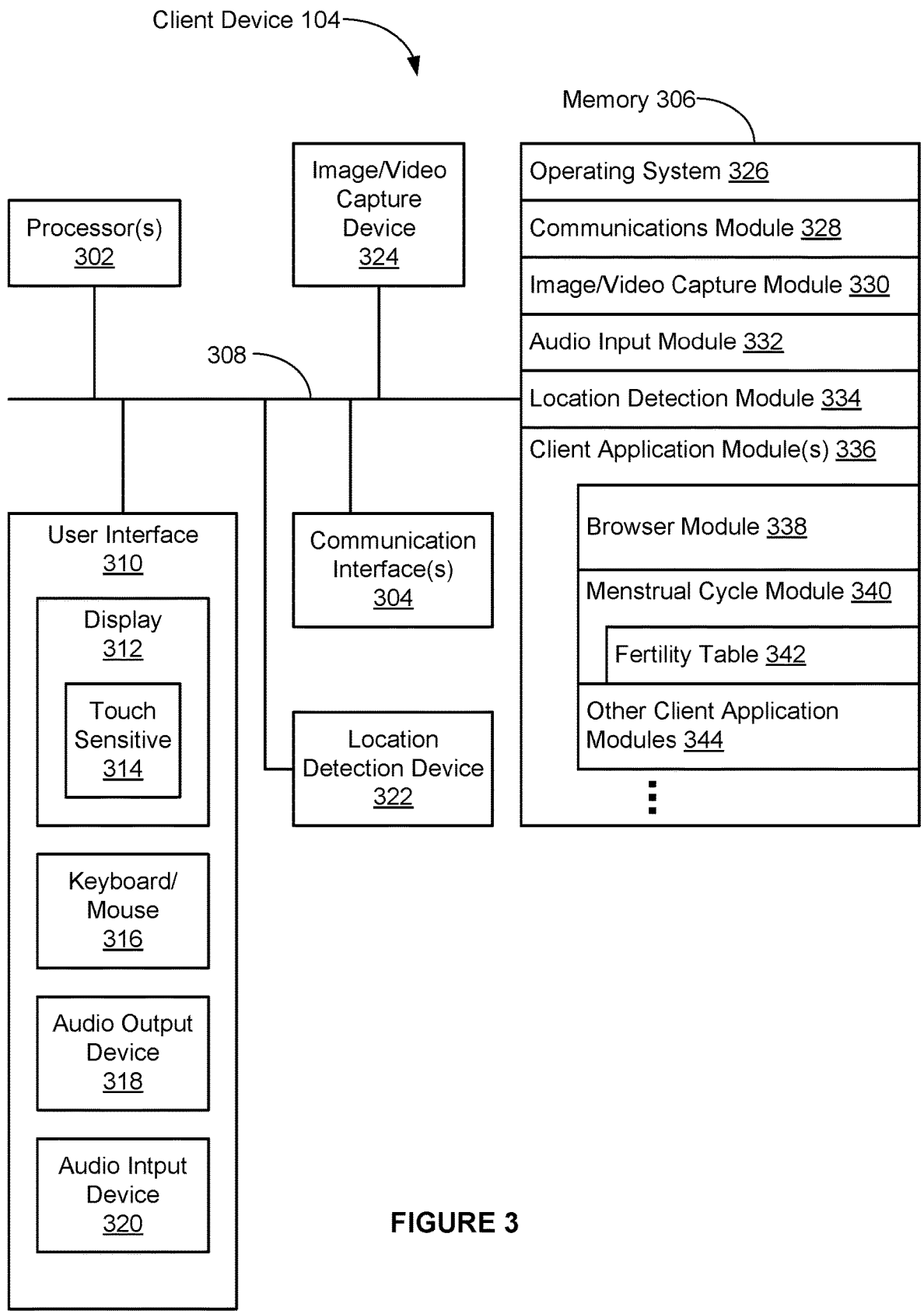
FIG. 3 is a block diagram illustrating an exemplary client device in accordance with some embodiments.

FIG. 3 is a block diagram illustrating an exemplary client device 104 in accordance with some embodiments. The client device 104 typically includes one or more processing units (processors or cores) 302, one or more network or other communications interfaces 304, memory 306, and one or more communication buses 308 for interconnecting these components. The communication buses 308 optionally include circuitry (sometimes called a chipset) that interconnects and controls communications between system components. The client device 104 includes a user interface 310. The user interface 310 typically includes a display device 312. In some embodiments, the client device 104 includes inputs such as a keyboard, mouse, and/or other input buttons 316. Alternatively or in addition, in some embodiments, the display device 312 includes a touch-sensitive surface 314, in which case the display device 312 is a touch-sensitive display. In client devices that have a touch-sensitive display 312, a physical keyboard is optional (e.g., a soft keyboard may be displayed when keyboard entry is needed). The user interface 310 also includes an audio output device 318, such as speakers or an audio output connection connected to speakers, earphones, or headphones. Furthermore, some client devices 104 use a microphone and voice recognition to supplement or replace the keyboard. Optionally, the client device 104 includes an audio input device 320 (e.g., a microphone) to capture audio (e.g., speech from a user). Optionally, the client device 104 includes a location detection device 322, such as a GPS (global positioning satellite) or other geo-location receiver, for determining the location of the client device 104. The client device 104 also optionally includes an image/video capture device 324, such as a camera or web cam.

Memory 306 includes high-speed random-access memory, such as DRAM, SRAM, DDR RAM or other random-access solid-state memory devices; and may include non-volatile memory, such as one or more magnetic disk storage devices, optical disk storage devices, flash memory devices, or other non-volatile solid-state storage devices. Memory 306 may optionally include one or more storage devices remotely located from the processor(s) 302. Memory 306, or alternately the non-volatile memory device(s) within memory 306, includes a non-transitory computer-readable storage medium. In some embodiments, memory 306 or the computer-readable storage medium of memory 306 stores the following programs, modules and data structures, or a subset or superset thereof:

- an operating system 326 that includes procedures for handling various basic system services and for performing hardware dependent tasks;
- a network communication module 328 that is used for connecting the client device 104 to other computers via the one or more communication network interfaces 304 (wired or wireless) and one or more communication networks, such as the Internet, cellular telephone networks, mobile data networks, other wide area networks, local area networks, metropolitan area networks, and so on;
- an image/video capture module 330 (e.g., a camera module) for processing a respective image or video captured by the image/video capture device 324, where the respective image or video may be sent or streamed (e.g., by a client application module 336) to the server system 108;
- an audio input module 332 (e.g., a microphone module) for processing audio captured by the audio input device 320, where the respective audio may be sent or streamed (e.g., by a client application module 336) to the server system 108;
- a location detection module 334 (e.g., a GPS, Wi-Fi, or hybrid positioning module) for determining the location of the client device 104 (e.g., using the location detection device 322) and providing this location information for use in various applications (e.g., social network client module 340); and
- one or more client application modules 336, including the following modules (or sets of instructions), or a subset or superset thereof:
  - a web browser module 338 (e.g., Internet Explorer by Microsoft, Firefox by Mozilla, Safari by Apple, or Chrome by Google) for accessing, viewing, and interacting with web sites for estimating fertility and tracking menstrual cycle information (e.g., services provided by a server system 108),
  - a menstrual cycle module 340 for estimating fertility, tracking menstrual cycle information, and accessing other related features, which includes:
    - a fertility table 342 for storing relative estimated fertilities for days and/or stages of a menstrual cycle; and/or
  - other optional client application modules 344, such as applications for word processing, fertility monitoring, calendaring, mapping, weather, stocks, time keeping, virtual digital assistant, presenting, number crunching (spreadsheets), drawing, instant messaging, e-mail, telephony, video conferencing, photo management, video management, a digital music player, a digital video player, 2D gaming, 3D (e.g., virtual reality) gaming, electronic book reader, and/or workout support.

Each of the above identified modules and applications correspond to a set of executable instructions for performing one or more functions as described above and/or in the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various embodiments. In some embodiments, memory 206 and/or 306 store a subset of the modules and data structures identified above. Furthermore, memory 206 and/or 306 optionally store additional modules and data structures not described above.

Attention is now directed towards embodiments of graphical user interfaces ("GUIs") and associated processes that may be implemented on a client device (e.g., the client device 104 in FIG. 3).

FIGS. 4A-4E illustrate exemplary GUIs on a client device 104 for estimating fertility and tracking menstrual cycle information, in accordance with some embodiments. The GUIs in these figures are used to illustrate the processes described below, including the method 500 (FIGS. 5A-5B). While FIGS. 4A-4E illustrate examples of GUIs, in other embodiments, one or more GUIs displays user-interface elements in arrangements distinct from the embodiments of FIGS. 4A-4E. The GUIs shown in FIGS. 4A-4H may be provided by a web browser (e.g., browser module 338, FIG. 3), a menstrual cycle application (e.g., menstrual cycle module 340), and/or a third-party application (e.g., client application module 344).

Figure 4A:
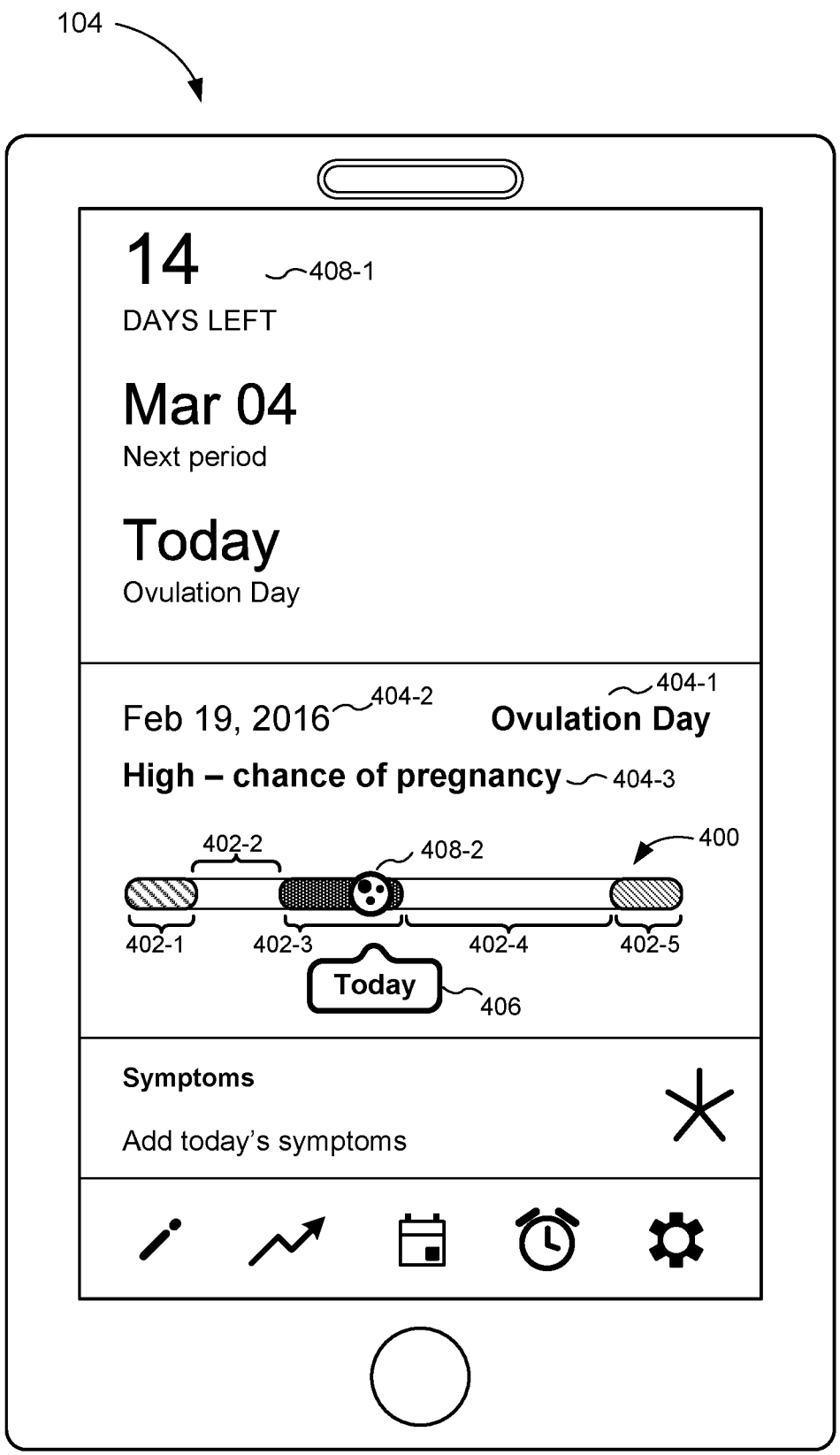
FIGS. 4A-4E illustrate exemplary user interfaces on a client device for estimating fertility and tracking menstrual cycle information, in accordance with some embodiments.
Figure 5A:
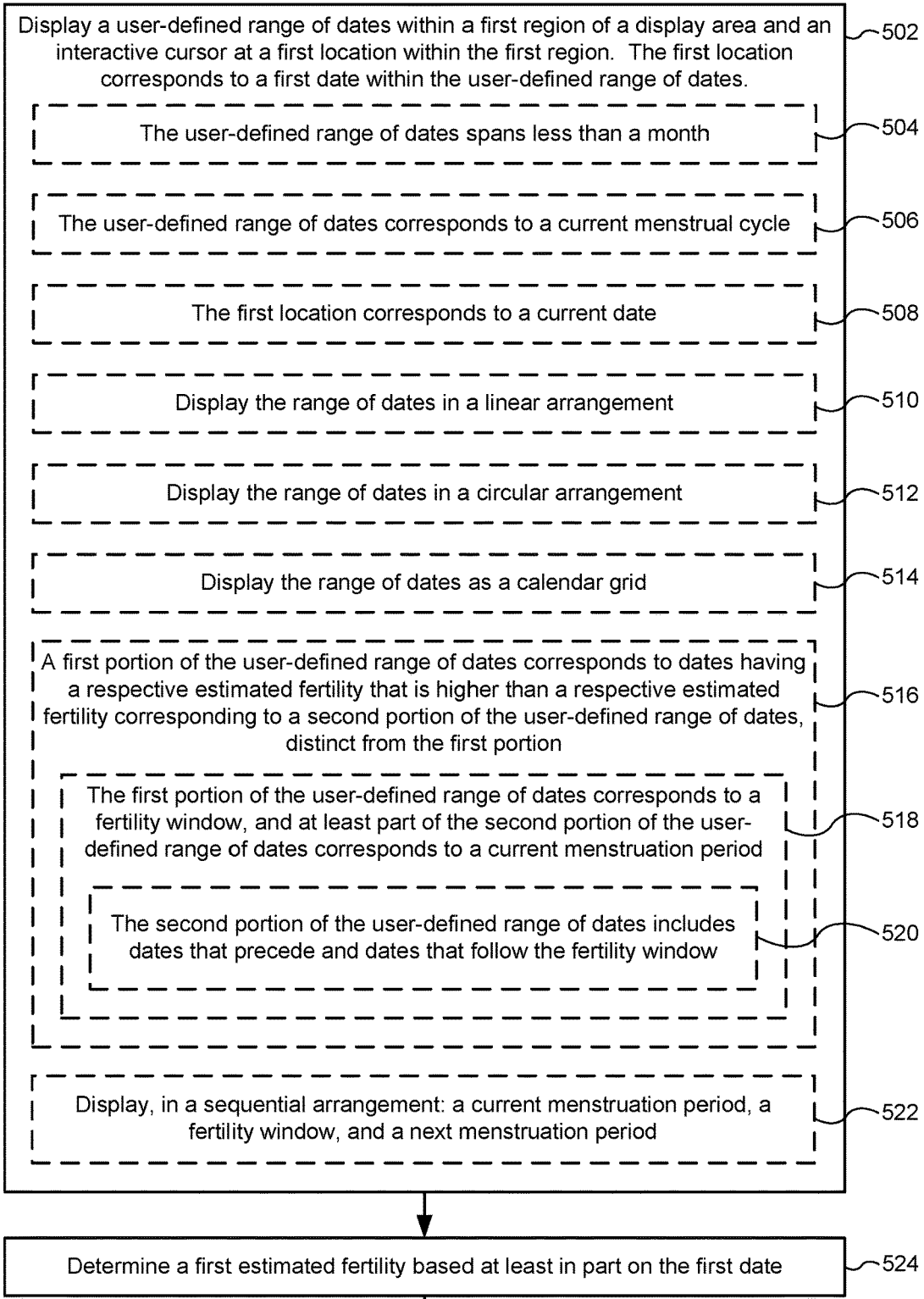
FIGS. 5A-5B are flow diagrams illustrating a method of estimating fertility and tracking menstrual cycle information, in accordance with some embodiments.
Figure 5B:
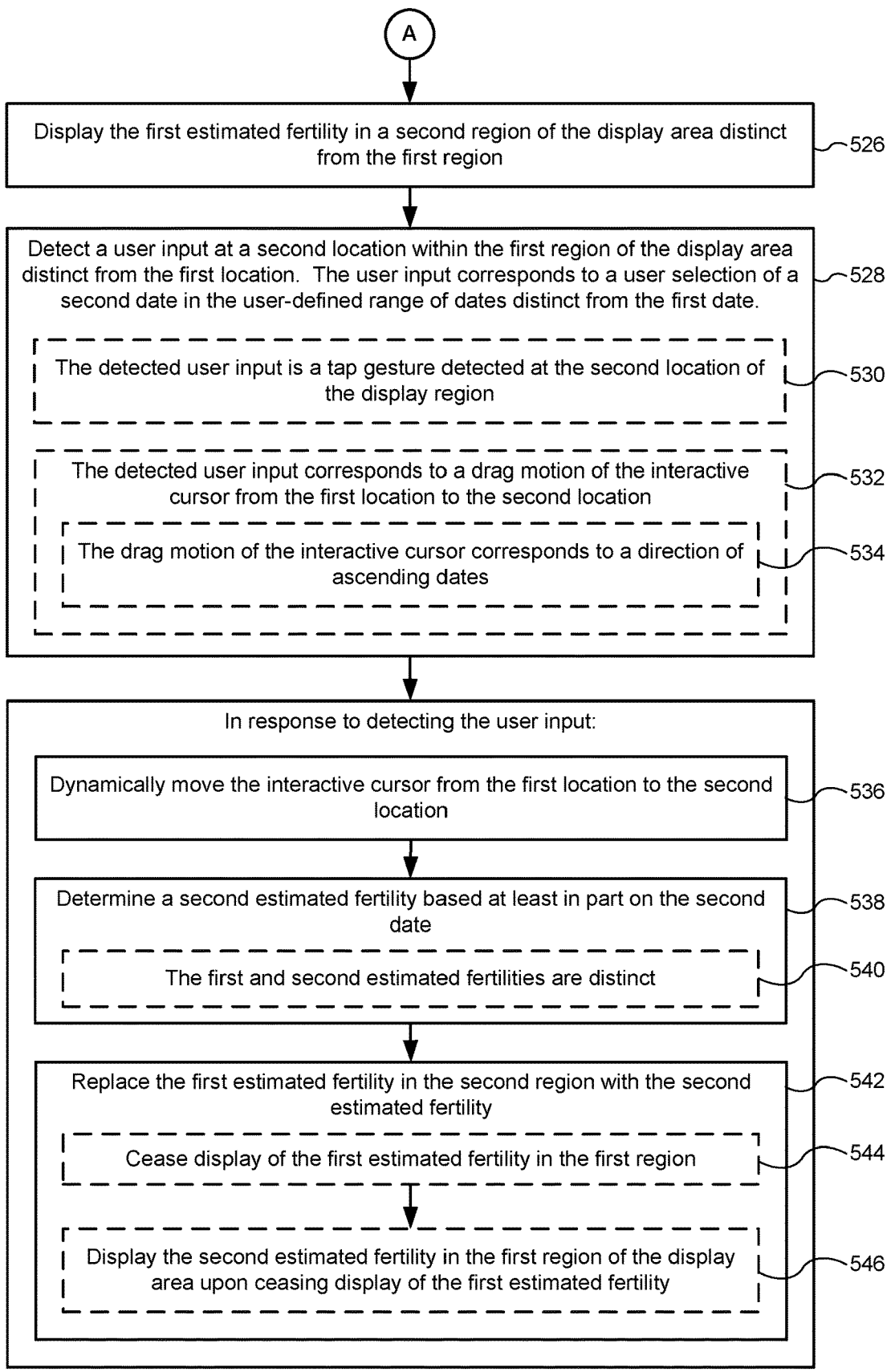

FIG. 4A illustrates a GUI for estimating fertility and tracking menstrual cycle information. As shown, a range of dates 400 is displayed within a respective region of a display area on the client device 104. The range of dates 400 is user-defined in that a user may define a range of a current menstrual cycle (e.g., a number of days, dates on which range begins and ends) by specifying (e.g., through an initial setup or settings of the menstrual cycle module 340) a first date on which the user's menstrual cycle commenced (i.e., date corresponding to the first day of the user's period), in addition to a duration of the user's menstrual cycle (e.g., typically lasting 28 days measured from the first day of the user's period). Once defined, the range of dates 400 corresponds to and represents the entire duration of the user's menstrual cycle, as defined by the user (optionally, as shown in FIG. 4A, the range of dates 400 corresponds to and represents the entire duration of the user's menstrual cycle in addition to the duration of the next predicted period, corresponding to portion 402-5).

As shown in FIG. 4A, the range of dates 400 is composed of multiple stages of the user-defined menstrual cycle. Each of the portions 402-1 through 402-5 represents a respective stage of a user-defined menstrual cycle, and comprises one or more days/dates within the user-defined range of dates 400. Stages of a menstrual cycle include a current menstruation period (e.g., corresponding to portion 402-1), an ovulation stage (e.g., corresponding to portion 402-3) and a next menstruation period (e.g., corresponding to portion 402-5). The portions representing different stages of the menstrual cycle may be visually distinct from one another, as shown by the varied shading among portions 402-1, 402-3, and 402-5, for example. Labels for the different stages of the menstrual cycle (e.g., "Period day . . . ," "Fertility Window," "Ovulation Day," "Next Period," . . . ) may also be predefined and displayed in a respective region of the display area (e.g., region 404-1).

Each of these stages and corresponding portions 402 (and optionally, each of the days within the respective portions 402) correspond to respective degrees of fertility generally indicating the likelihood of pregnancy on a particular date/range of dates. To allow users to track and estimate fertility on a particular day/date of a current menstrual cycle, an interactive cursor 406 may be moved (e.g., via a user input detected on the display of the client device 104) to a location along the displayed range of dates 400. The day/date corresponding to the location (or position) at which the interactive cursor 406 is detected is then used to determine an estimated fertility for display. As shown, various types of information regarding a user's menstrual cycle are shown within respective regions of a display area on the client device 104. For example, based on a current position of the interactive cursor 406 with respect to the range of dates 400, the GUI in FIG. 4A displays: a date corresponding to a current position of the interactive cursor 406 (e.g., "Feb. 19, 2016" displayed in region 404-2), a corresponding estimated fertility (e.g., "High-chance of pregnancy" displayed in region 404-3), and a corresponding stage of the menstrual cycle defined by the range of dates 400 (e.g., "Ovulation Day" displayed in region 404-1). Also displayed are an indicator for a number of days remaining until a next menstruation period (e.g., indicator 408-1, "14 Days Left"), and an indicator corresponding to one or more days of peak ovulation in the current menstrual cycle (e.g., indicator 408-2).

As described and illustrated in greater detail below, as the interactive cursor 406 is moved (e.g., via a user input) along the range of dates 400 from one location to another, the region of the display for displaying a corresponding estimated fertility (e.g., region 404-3) is replaced with an estimated fertility for a date corresponding to a current location of the interactive cursor 406. The estimated fertility is continually updated (e.g., if the estimated fertility changes from one location to the next) in accordance with the continued detection of a user input manipulating the interactive cursor 406.

Figure 4B:
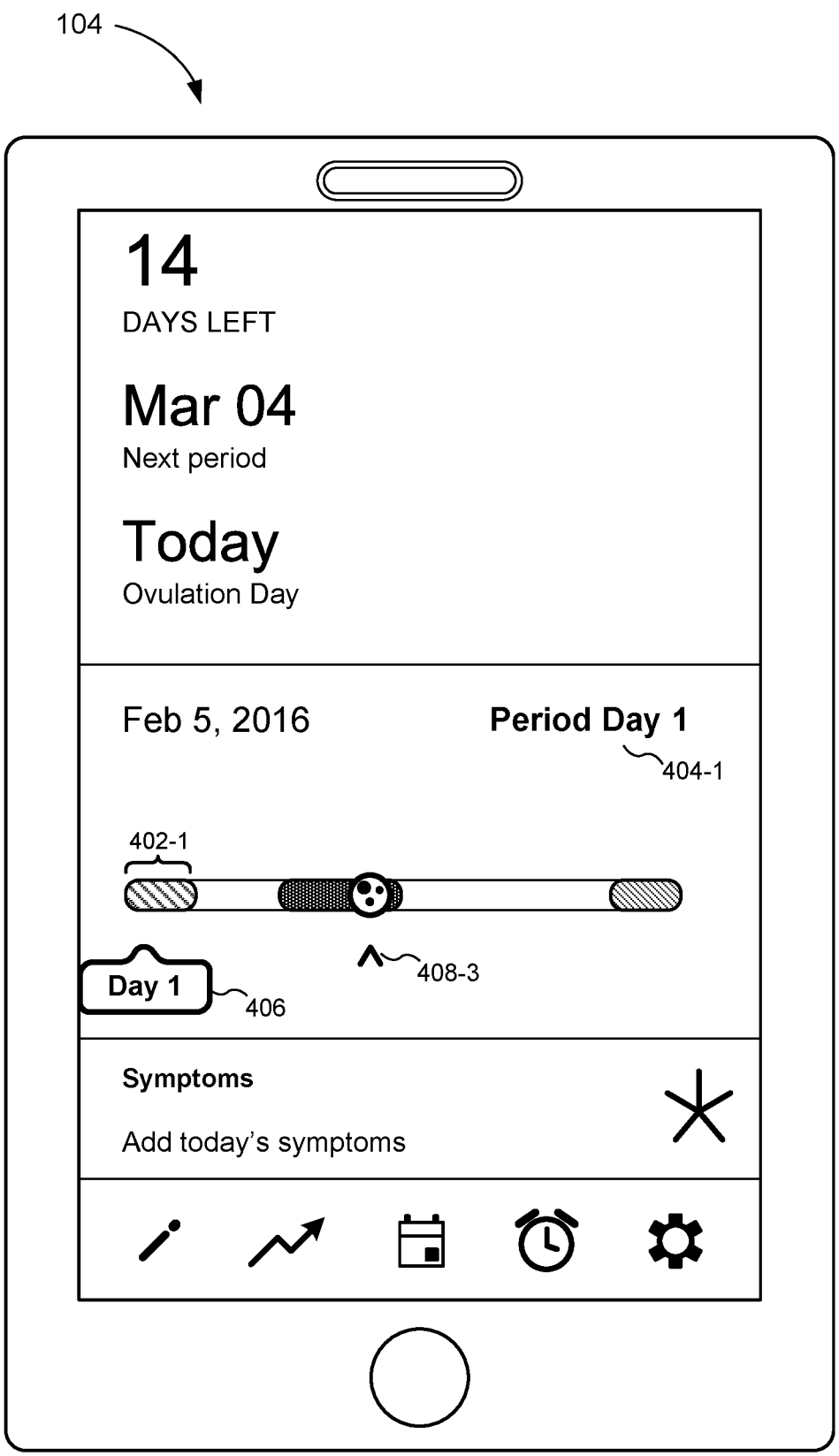

Referring now to FIG. 4B, in some embodiments, the interactive cursor 406 also indicates a relative position of a corresponding date with respect to the user-defined range of dates 400 (e.g., Day 1 of the current menstrual cycle, which corresponding to Feb. 5, 2016). In some embodiments, an indicator (e.g., 408-3) is also displayed which marks a location on the range of dates 400 corresponding to the current date (e.g., in this example, the current date is Feb. 19, 2016, as illustrated in FIG. 4A). In FIG. 4B, the corresponding stage of the menstrual cycle based on the current location/position of the interactive cursor 406 is "Period day 1" (i.e., the first day of the current menstruation period).

Figure 4C:
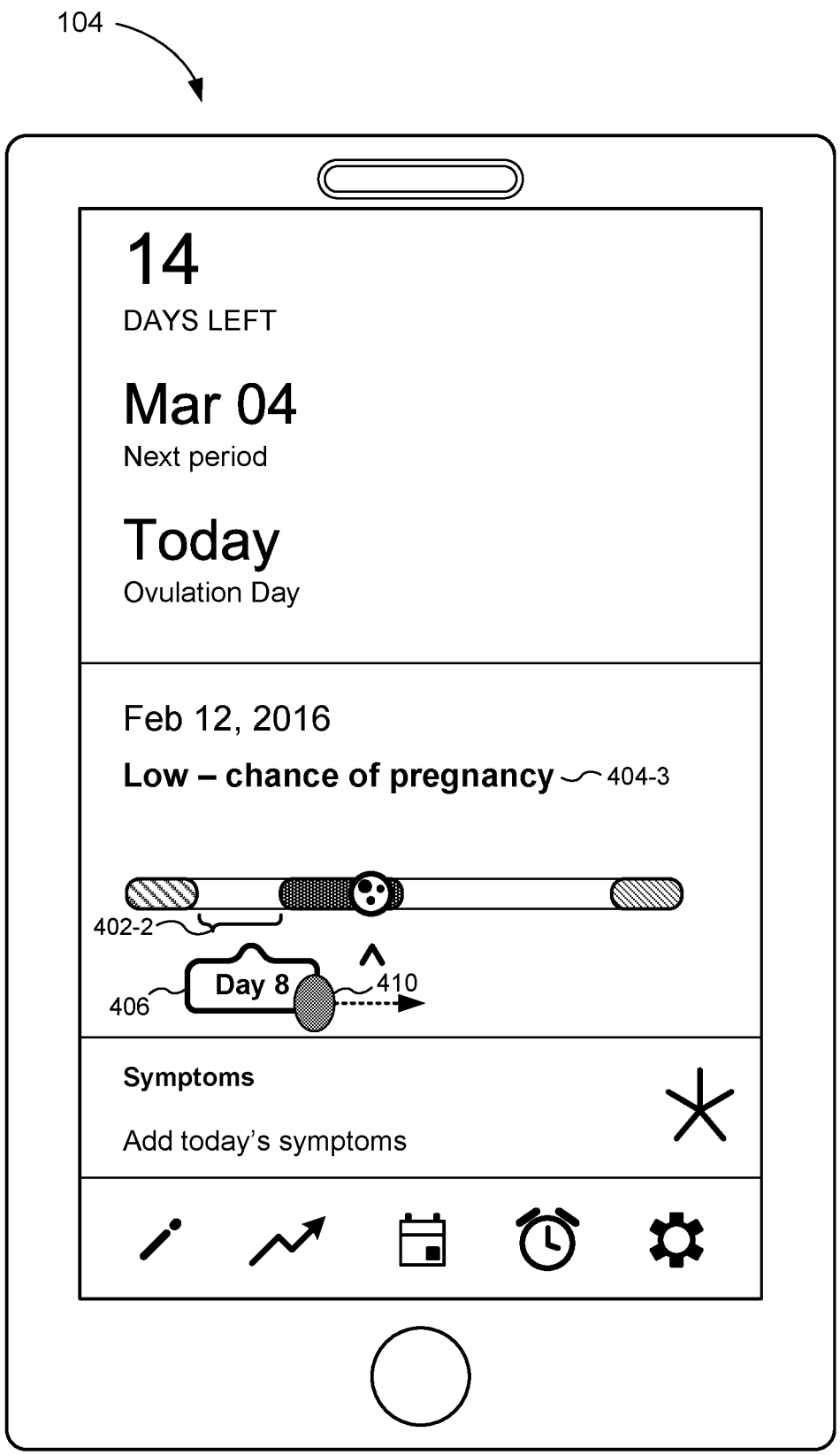
Figure 4D:
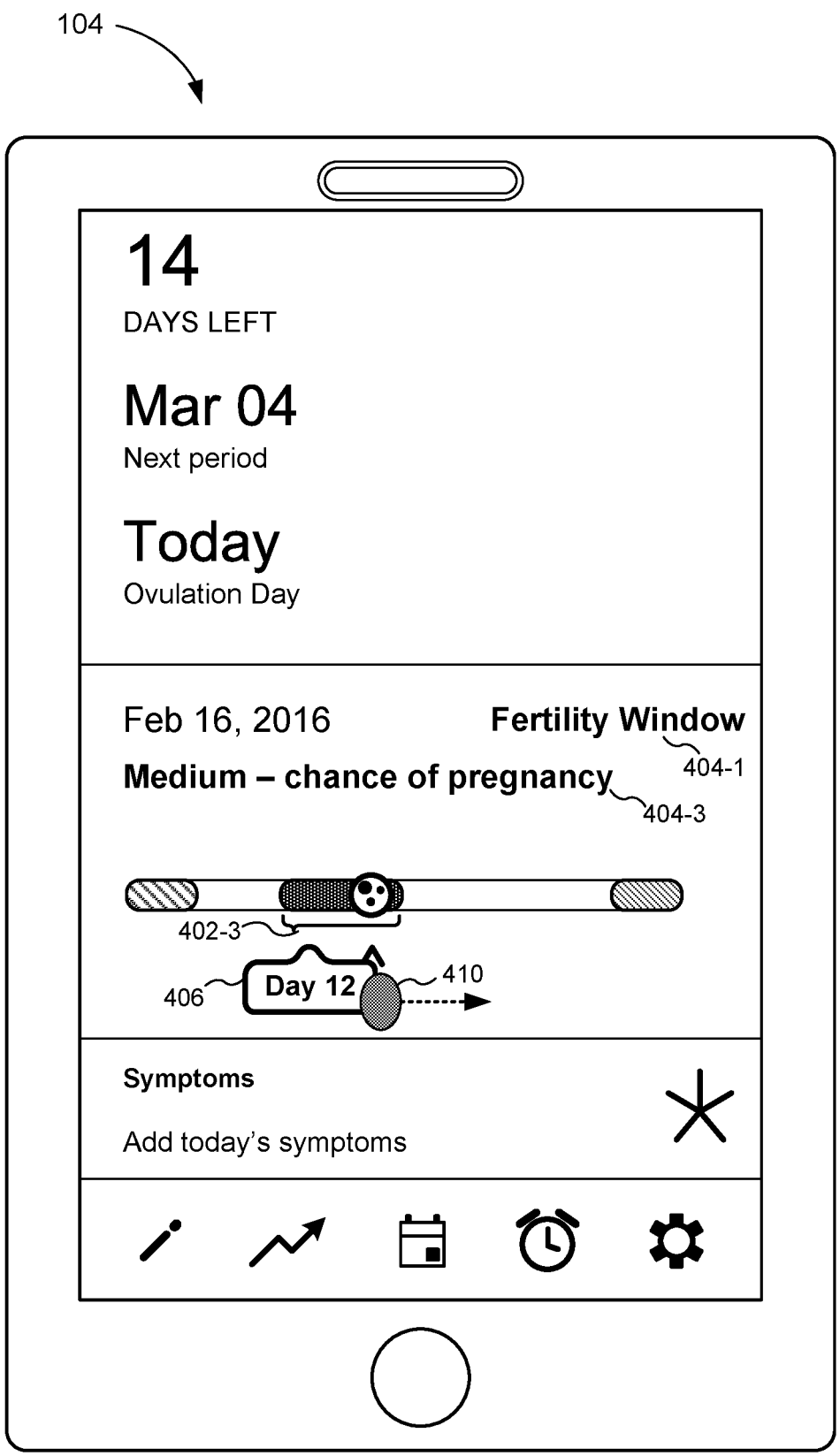
Figure 4E:
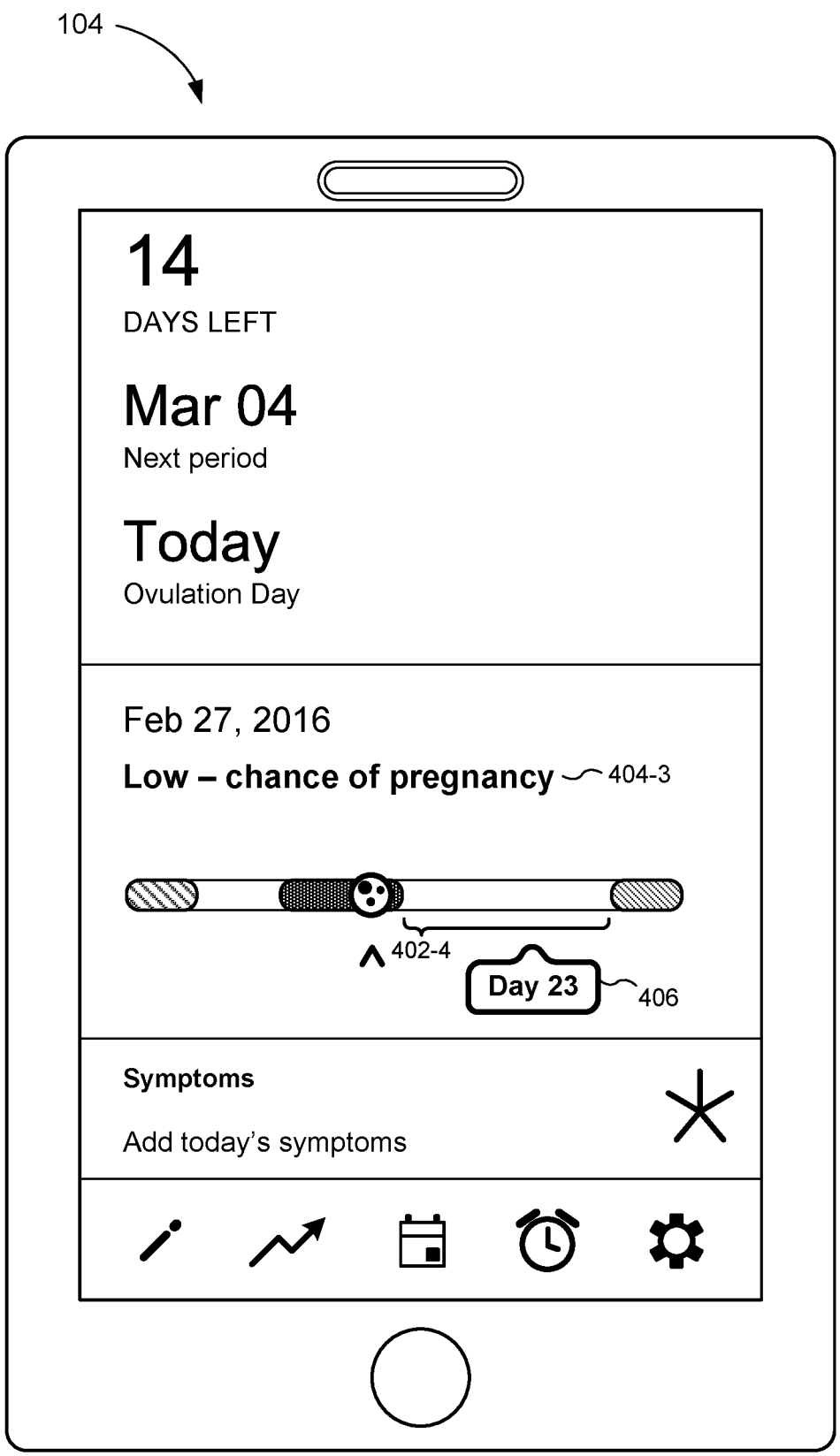

FIGS. 4C through 4E illustrate a sequence in which the interactive cursor 406 is moved across different locations along the range of dates 400, where the estimated fertility is updated at each of the different locations. As shown in FIG. 4C, the current location/position of the interactive cursor 406 is within the portion 402-2 of the range of dates 400 (e.g., "Day 8" of the current menstrual cycle, corresponding to Feb. 12, 2016), where the corresponding estimated fertility is low (e.g., "Low-chance of pregnancy"). Here, a user input 410 is detected (e.g., a drag gesture to the right), moving the interactive cursor 406 to the right. Referring now to FIG. 4D, in response the user input 410, the interactive cursor 406 is detected at a new location along the range of dates 400, indicating selection of another date for which a corresponding fertility is to be estimated and displayed. Here, the current location/position of the interactive cursor 406 is within the portion 402-3 of the range of dates 400 (e.g., "Day 12" of the current menstrual cycle, corresponding to a date within the ovulation stage of the menstrual cycle ("Fertility Window")). Accordingly, the fertility (displayed in region 404-3) is updated with the corresponding estimated fertility (e.g., "Medium-chance of pregnancy"). Upon continued detection of the user input 410 (i.e., continued drag motion), the fertility is updated based on a date corresponding to an updated location of the interactive cursor 406. For instance, referring to FIG. 4E, the current location/position of the interactive cursor 406 is within the portion 402-4 of the range of dates 400 (e.g., "Day 23" of the current menstrual cycle, corresponding to future date Feb. 27, 2016). Accordingly, the displayed fertility is updated with the corresponding estimated fertility (e.g., "Low-chance of pregnancy").

As shown in the foregoing examples, in some embodiments, all dates comprising a respective portion of the range of dates 400 have the same respective estimated fertility (e.g., all dates comprising portion 402-2 have a low estimated fertility). In some embodiments, a respective portion of the range of dates 400 includes dates together having at least two distinct estimated fertilities (e.g., for portion 402-3 ("Fertility Window"), the estimated fertility for February 19 is high (FIG. 4A), while the estimated fertility for February 16 is medium (FIG. 4D)).

The examples shown in FIGS. 4A-4E illustrate one particular arrangement of user interface elements (e.g., range of dates 400, regions for estimated fertility, menstrual cycle stage, etc.) on a GUI for determining and providing menstrual cycle information. In other embodiments, user interface elements may be displayed in an arrangement distinct from the examples of FIGS. 4A-4E and may include additional and/or alternative user interface elements or information.

FIGS. 5A-5B are flow diagrams illustrating method 500 for estimating fertility and tracking menstrual cycle information, in accordance with some embodiments. Steps of the method 500 may be performed on a client device (e.g., client device 104, FIGS. 1 and 3) and/or other electronic devices or systems (e.g., server system 108, FIG. 2). FIGS. 5A-5B correspond to instructions stored in a computer memory (e.g., memory 306 of the client device 104, FIG. 3) or other computer-readable storage medium. To assist with describing the method 500, FIGS. 5A-5B will be described with reference to the exemplary GUIs illustrated in FIGS. 4A-4E.

In performing the method 500, the client device displays a user-defined range of dates within a first region of a display area and an interactive cursor at a first location within the first region. The first location corresponds to a first date within the user-defined range of dates (e.g., range of dates 400 displayed within a first region and interactive cursor 406 at a first location corresponding to "Day 8" (Feb. 12, 2016) of the range of dates, FIG. 4C). In some embodiments, the user-defined range of dates spans less than a month (504) (e.g., portions 402-1 through 402-4, which together span 28 days). In some implementations, the user-defined range of dates corresponds to a single menstrual cycle and a next menstruation period (e.g., in FIG. 4A, the range of dates 400 includes portions 402-1 through 402-4 which correspond to a current menstrual cycle, and also includes portion 402-5 which corresponds to a next menstrual period).

In some embodiments, the user-defined range of dates corresponds to a current menstrual cycle (506) (e.g., range of dates 400 in FIG. 4A, which corresponds to a current menstrual cycle spanning dates that includes a current date). In some embodiments, a first boundary of the first region within which the user-defined range of dates is displayed corresponds to a beginning date of the current menstrual cycle (e.g., leftmost boundary of portion 402-1, FIG. 4B), and a second boundary of the first region, opposite the first boundary, corresponds to both an end date of the current menstrual cycle and a start date of a next menstrual cycle (e.g., rightmost boundary of portion 402-4, FIG. 4A).

In some embodiments, the first location corresponds to a current date (e.g., the location of interactive cursor 406 corresponds to a current date ("Today"), FIG. 4A). In some implementations, the interactive cursor is displayed at the first location corresponding to the current date upon initialization of an application that performs the method 500 (e.g., default location of the interactive cursor corresponds to a current date when the menstrual cycle module 340 is executed).

In some embodiments, displaying (502) the user-defined range of dates includes displaying (510) the range of dates in a linear arrangement (e.g., range of dates 400 displayed in a line, FIG. 4A). In some embodiments, displaying (502) the user-defined range of dates includes displaying (512) the range of dates in a circular arrangement (e.g., dates are arranged along a circle, with the dates ascending/descending in a clock-wise direction). In some embodiments, displaying (502) the user-defined range of dates includes displaying (514) the range of dates as a calendar grid. In some embodiments, the interactive cursor further indicates a relative position of a corresponding date with respect to the user-defined range of dates (e.g., in FIG. 4D, the interactive cursor 406 indicates that its location corresponds to "Day 12" of a current menstrual cycle).

In some embodiments, a first portion of the user-defined range of dates corresponds (516) to dates having a respective estimated fertility that is higher than a respective estimated fertility corresponding to a second portion of the user-defined range of dates, distinct from the first portion. As an example, portion 402-2 of the range of dates 400 (FIG. 4C) corresponds to one or more dates having a low estimated fertility (e.g., Day 8, Feb. 12, 2016), whereas portion 402-3 of the range of dates 400 (FIG. 4D) corresponds to one or more dates having a medium estimated fertility (e.g., Day 12, Feb. 16, 2016). In some implementations, the first portion of the user-defined range of dates corresponds (518) to a fertility window (e.g., portion 402-3, FIG. 4D), and at least part of the second portion of the user-defined range of dates corresponds to a current menstruation period (e.g., portion 402-1, FIG. 4B). Furthermore, in some implementations, the second portion of the user-defined range of dates includes (520) dates that precede and dates that follow the fertility window (e.g., portions 402-1 and 402-2 precede a fertility window corresponding to portion 402-3, and portions 402-4 and 402-5 follow the fertility window). In some embodiments, the first date corresponds to a date within the second portion of the user-defined range of dates (e.g., in FIG. 4C, Day 8 of portion 406, corresponding to low estimated fertility), and the second date corresponds to a date within the first portion of the user-defined range of dates (e.g., in FIG. 4D, Day 12 of portion 402-3, corresponding to medium estimated fertility).

In some embodiments, displaying (502) the user-defined range of dates includes displaying (522), in a sequential arrangement: a current menstruation period (e.g., portion 402-1, FIG. 4A), a fertility window (e.g., portion 402-3, FIG. 4A), and a next menstruation period (e.g., portion 402-5, FIG. 4A). In some embodiments, displaying (502) the fertility window comprises displaying an indicator corresponding to one or more days of peak ovulation (e.g., 408-2, FIG. 4A).

A first estimated fertility is determined (524) based at least in part on the first date. Estimations of fertility may be based on statistical information that indicates relative fertility with respect to specific days or periods of time of a menstrual cycle. As an example, the menstruation period (marking the beginning of a menstrual cycle) typically lasts the first 5 days of a menstrual cycle, while ovulation (e.g., "fertility window") begins on day 11 and lasts until day 18 of the menstrual cycle. These various stages of a menstrual cycle, and optionally the days within each of the stages, have respective estimated fertilities (e.g., relative days/stages of a menstrual cycle and their corresponding estimated fertilities being stored in a fertility table 342 (FIG. 3) or other data structure). Thus, in some embodiments, by identifying and using the date that corresponds to a current location of an interactive cursor, an estimated fertility may be determined (e.g., using the relative day within a menstrual cycle in searching the fertility table 342 described above). For example, in FIG. 4C, a location of the interactive cursor 406 corresponds to the eighth day of a menstrual cycle, the eighth day having a low estimated fertility (e.g., based on stored entries of a fertility table). Other data or factors may be used in determining an estimated fertility (e.g., user specific medical information that adjusts default fertility data).

Referring now to FIG. 5B, the first estimated fertility is displayed (526) in a second region of the display area distinct from the first region (e.g., in FIG. 4C, a low estimated fertility displayed in region 404-3).

In some embodiments, an indication of a respective stage of a current menstrual cycle is displayed in a third region of the display area (e.g., current menstruation period, an ovulation stage, a next menstruation period, etc.). The respective stage is determined based on a date within the user-defined range of dates to which a current location of the interactive cursor corresponds (e.g., "Fertility Window" indicates an ovulation stage of a current menstrual cycle, displayed in region 404-1, FIG. 4D).

A user input is detected (528) at a second location within the first region of the display area distinct from the first location. The user input corresponds to a user selection of a second date in the user-defined range of dates distinct from the first date. In some embodiments, the detected user input is (530) a tap gesture detected at the second location of the display region. In some embodiments, the detected user input corresponds (532) to a drag motion of the interactive cursor from the first location to the second location. For example, referring to FIGS. 4C and 4D, a user input 410 is detected on the interactive cursor 406 that corresponds to drag motion from a first location and date (e.g., Day 8, Feb. 12, 2016) to a second location and date (e.g., Day 12, Feb. 16, 2016). In some embodiments, the drag motion of the interactive cursor corresponds (534) to a direction of ascending dates (e.g., in FIG. 4C, direction of the user input 410 corresponds to direction in which dates ascend).

In response to detecting the user input, the interactive cursor is dynamically moved (536) from the first location to the second location, and a second estimated fertility is determined based at least in part on the second date. Referring again to the example in FIG. 4D, the estimated fertility is updated based on the second date corresponding to the location of the interactive cursor 406 (e.g., twelfth day of a menstrual cycle, Feb. 16, 2016). Here, the twelfth day of a menstrual cycle has a medium estimated fertility. In some embodiments, the first and second estimated fertilities are distinct (540) (e.g., low estimated fertility in FIG. 4C, compared to a medium estimated fertility in FIG. 4D). Thereafter, the first estimated fertility is replaced (542) in the second region with the second estimated fertility (e.g., the fertility displayed in region 404-3 is updated to indicate a medium estimated fertility, FIG. 4D). In some embodiments, replacing (542) the first estimated fertility in the second region includes ceasing (544) display of the first estimated fertility in the first region and displaying (546) the second estimated fertility in the first region of the display area upon ceasing display of the first estimated fertility.

In some embodiments, a continuation of the user input is detected, wherein the detected continuation corresponds to selection of a third date in the user-defined range of dates (e.g., from FIG. 4D to 4E, the user input 410 continues then ceases, and a location of the interactive cursor corresponds to Day 23). While detecting the continuation of the user input, a third estimated fertility is determined, and the second estimated fertility is replaced in the second region with the third estimated fertility (e.g., the fertility displayed in region 404-3 is updated to reflect a low estimated fertility). Thus, in some embodiments, as a user input dynamically moves a position of the interactive cursor with respect to the range of dates, the estimated fertility is iteratively updated based on a current location of the interactive cursor with respect to the user-defined range of dates.

For situations in which the systems discussed above collect information about users, the users may be provided with an opportunity to opt in/out of programs or features that may collect personal information (e.g., information about a user's preferences or a user's contributions to social content providers). In addition, in some embodiments, certain data may be anonymized in one or more ways before it is stored or used, so that personally identifiable information is removed. For example, a user's identity may be anonymized so that the personally identifiable information cannot be determined for or associated with the user, and so that user preferences or user interactions are generalized (for example, generalized based on user demographics) rather than associated with a particular user.

Although some of various drawings illustrate a number of logical stages in a particular order, stages which are not order dependent may be reordered and other stages may be combined or broken out. While some reordering or other groupings are specifically mentioned, others will be apparent to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

What is claimed is:

1. A method, comprising:
an electronic device having a graphical user interface comprising a first region, a second region, a third region and a fourth region, one or more processors and memory storing instructions for execution by the one or more processors:
displaying a user-defined range of dates within the first region of a display area and an interactive cursor at a first location within the first region, the first location corresponding to a first date within the user-defined range of dates, wherein the user-defined range of dates comprises displaying the range of dates in a single straight line and includes multiple portions of a current menstrual cycle and at least one portion of a next menstrual cycle;
based at least in part on the first location of the first date within the user-defined range of dates, identifying one of the multiple portions of the current menstruation cycle corresponding to the first date and determining a first estimated fertility according to the first location of the interactive cursor within the identified portion of the current menstruation cycle;
displaying the first estimated fertility in the second region of the display area distinct from the first region;
detecting a user input at a second location within the first region of the display area distinct from the first location, the user input corresponding to a user selection of a second date in the user-defined range of dates distinct from the first date, and the first date and the second date are within the same identified portion of the current menstrual cycle;
in response to detecting the user input:
dynamically moving the interactive cursor from the first location to the second location;
determining a second estimated fertility that is different from the first estimated fertility according to the second location of the interactive cursor within the same identified portion of the current menstrual cycle;
replacing the first estimated fertility in the second region with the second estimated fertility;
displaying a label for different stages of the current menstrual cycle in the second region of the display area; and
concurrently displaying an indicator for a number of days remaining until the next menstrual cycle in a third region of the display area and concurrently displaying an ovulation indication corresponding to one or more days of peak ovulation in the current menstrual cycle in the third region of the display area, wherein the third region is distinct from the first region, the second region, and the fourth region;
and displaying a user-defined symptom in a user symptom input region of the fourth region, wherein the first region, the second region, the third region and the fourth are simultaneously and nonoverlappingly displayed.

2. The method of claim 1, wherein the user-defined range of dates spans less than a month.

3. The method of claim 1, wherein:
a leftmost portion of the first region within which the user-defined range of dates is displayed corresponds to a menstrual period of the current menstrual cycle, and a rightmost portion of the first region, opposite the leftmost portion, corresponds to a menstrual period of the next menstrual cycle.

4. The method of claim 1, wherein the identified portion of the current menstruation cycle corresponds to dates having a respective estimated fertility that is higher than a respective estimated fertility corresponding to a second portion of the current menstruation cycle, distinct from the identified portion of the current menstruation cycle.

5. The method of claim 4, wherein the identified portion of the current menstruation cycle corresponds to a fertility window having at least two different estimated fertilities, and the second portion of the current menstruation cycle corresponds to a same estimated fertility.

6. The method of claim 5, wherein the second portion of the current menstruation cycle includes dates that precede or dates that follow the fertility window.

7. The method of claim 1, wherein the detected user input is a tap gesture detected at the second location of the display region.

8. The method of claim 1, wherein the detected user input corresponds to a drag motion of the interactive cursor from the first location to the second location.

9. The method of claim 8, further comprising:
detecting a continuation of the user input, wherein the detected continuation corresponds to selection of a third date in the user-defined range of dates;
while detecting the continuation of the user input:
determining a third estimated fertility; and
replacing the second estimated fertility in the second region with the third estimated fertility.

10. The method of claim 8, wherein the drag motion of the interactive cursor corresponds to a direction of ascending dates.

11. The method of claim 1, wherein the first location corresponds to a current date.

12. The method of claim 1, wherein the first and second estimated fertilities are distinct.

13. The method of claim 1, wherein the interactive cursor further indicates a relative position of a corresponding date with respect to the user-defined range of dates.

14. The method of claim 1, wherein replacing the first estimated fertility in the second region comprises:
ceasing display of the first estimated fertility in the first region; and
upon ceasing display of the first estimated fertility, displaying the second estimated fertility in the first region of the display area.

15. The method of claim 1, wherein the ovulation indication is determined based on a date within the user-defined range of dates to which a current location of the interactive cursor corresponds.

16. An electronic device, comprising:
a processor;
a graphical user interface comprising a first region, a second region, a third region and a fourth region; and
memory storing one or more programs for execution by the processor, the one or more programs including instructions for:
displaying a user-defined range of dates within the first region of a display area and an interactive cursor at a first location within the first region, the first location corresponding to a first date within the user-defined range of dates, wherein the user-defined range of dates comprises displaying the range of dates in a single straight line and includes multiple portions of a current menstrual cycle and at least one portion of a next menstrual cycle;
based at least in part on the first location of the first date within the user-defined range of dates, identifying one of the multiple portions of the current menstruation cycle corresponding to the first date and determining a first estimated fertility according to the first location of the interactive cursor within the identified portion of the current menstruation cycle;
displaying the first estimated fertility in the second region of the display area distinct from the first region;
detecting a user input at a second location within the first region of the display area distinct from the first location, the user input corresponding to a user selection of a second date in the user-defined range of dates distinct from the first date, and the first date and the second date are within the same identified portion of the current menstrual cycle;
in response to detecting the user input:
dynamically moving the interactive cursor from the first location to the second location;
determining a second estimated fertility that is different from the first estimated fertility according to the second location of the interactive cursor within the same identified portion of the current menstrual cycle;
replacing the first estimated fertility in the second region with the second estimated fertility;
displaying a label for different stages of the current menstrual cycle in the second region of the display area; and concurrently displaying an indicator for a number of days remaining until the next menstrual cycle in a third region of the display area and concurrently displaying an ovulation indication corresponding to one or more days of peak ovulation in the current menstrual cycle in the third region of the display area, wherein the third region is distinct from the first region, the second region, and the fourth region;
and displaying a user-defined symptom in a user symptom input region of the fourth region, wherein the first region, the second region, the third region and the fourth are simultaneously and nonoverlappingly displayed.

17. A non-transitory computer readable storage medium, storing one or more programs for execution by one or more processors, the one or more programs including instructions for:
displaying a user-defined range of dates within a first region of a display area and an interactive cursor at a first location within the first region, the first location corresponding to a first date within the user-defined range of dates, wherein the user-defined range of dates comprises displaying the range of dates in a single straight line and includes multiple portions of a current menstrual cycle and at least one portion of a next menstrual cycle;
based at least in part on the first location of the first date within the user-defined range of dates, identifying one of the multiple portions of the current menstruation cycle corresponding to the first date and determining a first estimated fertility according to the first location of the interactive cursor within the identified portion of the current menstruation cycle;
displaying the first estimated fertility in a second region of the display area distinct from the first region;

detecting a user input at a second location within the first region of the display area distinct from the first location, the user input corresponding to a user selection of a second date in the user-defined range of dates distinct from the first date, and the first date and the second date are within the same identified portion of the current menstrual cycle;

in response to detecting the user input:
dynamically moving the interactive cursor from the first location to the second location;
determining a second estimated fertility that is different from the first estimated fertility according to the second location of the interactive cursor within the same identified portion of the current menstrual cycle;

replacing the first estimated fertility in the second region with the second estimated fertility;

displaying a label for different stages of the current menstrual cycle in the second region of the display area; and concurrently displaying an indicator for a number of days remaining until the next menstrual cycle in a third region of the display area and concurrently displaying an ovulation indication corresponding to one or more days of peak ovulation in the current menstrual cycle in the third region of the display area, wherein the third region is distinct from the first region and the second region; and displaying a user-defined symptom in a user symptom input region of the fourth region, wherein the fourth region is distinct from the first region, the second region and the third region, and wherein the first region, the second region, the third region and the fourth region are simultaneously and nonoverlappingly displayed.

* * * * *